United States Patent [19]

Stevens

[11] 4,074,135
[45] Feb. 14, 1978

[54] GAMMA CAMERA IN WHICH ONLY THE THREE LARGEST SIGNALS ARE USED FOR POSITION DETERMINATION

[75] Inventor: Petrus Franciscus Stevens, Eindhoven, Netherlands

[73] Assignee: U.S. Philips Corporation, New York, N.Y.

[21] Appl. No.: 623,394

[22] Filed: Oct. 17, 1975

[30] Foreign Application Priority Data
Oct. 21, 1974 Netherlands .......................... 7413741

[51] Int. Cl.² .............................................. G01T 1/20
[52] U.S. Cl. .................................. 250/366; 250/363 S
[58] Field of Search ...................... 250/363 S, 366, 369

[56] References Cited
U.S. PATENT DOCUMENTS

| 3,732,419 | 5/1973 | Kulberg et al. | 250/363 S |
| 3,784,821 | 1/1974 | Jaszczak | 250/363 S |

*Primary Examiner*—Davis L. Willis
*Attorney, Agent, or Firm*—Frank R. Trifari

[57] ABSTRACT

A gamma camera in which the signals of the three detectors supplying the comparatively largest signals are used for the position determination of scintillations. As a result, the detection device has a simpler construction, can operate faster and a substantial improvement is achieved in regard to the signal-to-noise ratio of the signals used.

5 Claims, 3 Drawing Figures

GAMMA CAMERA IN WHICH ONLY THE THREE LARGEST SIGNALS ARE USED FOR POSITION DETERMINATION

The invention relates to a scintillation camera provided with a conversion member and a matrix of detectors adapted thereto for determining the value and the position of signals generated in the conversion member by radiation to be measured.

A scintillation camera of this kind is known, for example, from British Patent Specification 1,213,478. In cameras of this kind, besides the value also the position within the measuring field of signals generated in a conversion member is to be determined on the basis of the measuring pulses originating from the individual detectors. To this end, it is common practice to store the pulses of each of the detectors, to amplify each pulse in a different manner in order to compensate for their differences which are due to their different positions with respect to the conversion member, and to determine the coordinates of the scintillation pulse on the basis of all signals together by means of an electronic process. A system of this kind has the drawback that all detector signals are used for the position determination. The accuracy of the position determination is adversely affected by detectors supplying comparatively small signal, i.e., detectors which are situated comparatively far from the luminescence source, because of the poor signal-to-noise ratio.

The invention has for its object to provide a scintillation camera wherein this drawback is avoided. To this end, a camera of the kind set forth is characterized in that means are provided for selecting a sub-group of detectors on the basis of a signal to be supplied by the detectors.

By first selecting a comparatively small number of measuring pulses, for example, the three largest measuring pulses, from a series of measuring pulses from the various detectors, the detectors whose signals have a comparatively unfavourable signal-to-noise ratio are precluded from the position determination. The position determination can thus be more accurately performed.

A preferred embodiment according to the invention will be described in detail hereinafter with reference to the drawing.

Figure 1:
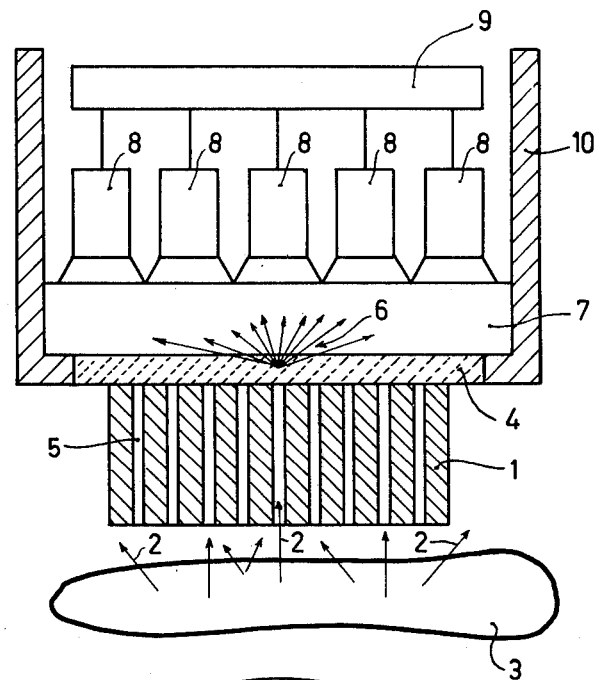
FIG. 1 is a diagrammatic longitudinal sectional view of a pick-up section of a commonly used gamma camera comprising a matrix of detectors.
Figure 2:
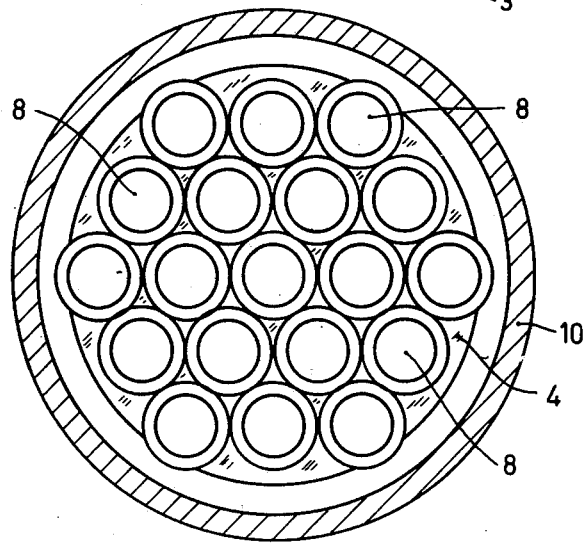
FIG. 2 shows the position of the detectors with respect to the scintillation crystal in such a camera.

A gamma camera as shown in FIG. 1 comprises a collimator 1 whereby a part of gamma quanta 2, for example, originating from an object 3 to be medically examined, is selected for measurement. To this end, the collimator is constructed, for example, as a comparatively thick lead disc comprising a large number of comparatively narrow ducts 5. These ducts may all extend in parallel, but may alternatively be oriented such that a focussing collimator is obtained. A gamma quantum which passes one of the ducts 5 reaches a conversion member 4 which is in this case constructed as a scintillation crystal in the form of a round disc having a diameter of, for example, 25 cm and a thickness of 1 cm. The gamma quantum is converted into a light pulse in the scintillation crystal. Using a similar construction, other nuclear particles or radiation can also be converted into light or at least into a radiation for which sensitive detectors are available. The scintillation light 6, having a wavelength which is preferably situated in the visible or near the visible (ultraviolet) range, is incident on detectors 8 via a light conductor 7. The sensitivity of the detectors is preferably adapted as well as possible to the wavelength of the scintillation light. The detectors 8 are constructed, for example, as photomultipliers or semiconductor detectors and are arranged opposite the conversion member 4 in a regular pattern. FIG. 2 shows a frequently used arrangement of the detectors 8. This arrangement results in a matrix of 19 detectors, the centres thereof being situated on three concentrical circles about a centrally situated detector. Matrices of 30 or 37 detectors are also used. It is to be noted that only a comparatively small part of the gamma quanta 2, i.e., only the part whose direction of incidence corresponds at least substantially to the duct direction, is intercepted by the scintillation crystal, but that all the scintillation light of all the intercepted gamma quanta is intercepted as well as possible by the detectors. Each of the detectors receives a more or less large fraction of the light produced from each scintillation pulse. All pulses supplied by the detectors are stored in a register 9 for further processing.

The camera is enveloped by a shield 10 which is preferably made of lead, like the collimator, and which serves to absorb the gamma quanta which pass the conversion member without being converted. At the same time the detectors 8 are shielded against external light by the shield 10.

Figure 3:
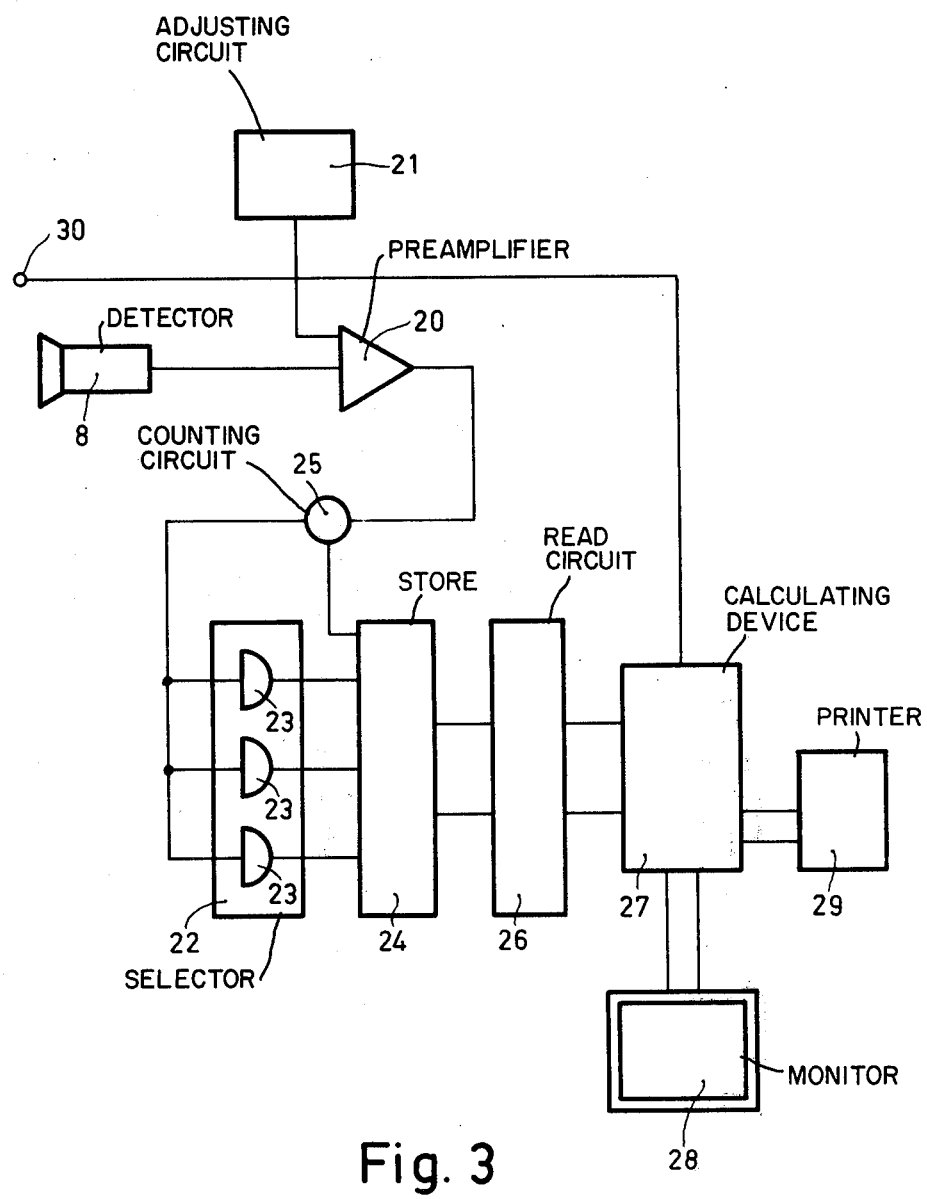
FIG. 3 shows a block diagram of the electrical circuit of a preferred embodiment of a scintillation camera according to the invention.

In accordance with the invention, a camera of the described type comprises a selection and storage unit, a preferred embodiment thereof being shown in FIG. 3.

Each detector has associated therewith a preamplifier 20 for amplifying the pulse supplied by the detector. Using an adjusting circuit 21, the gain factor of the preamplifiers can be adapted, for example, to the nature of the radiation to be used, for readjusting any drift in the detector or the preamplifier or, like in known cameras (see for example ISA Transactions 5, 1966, pages 327 and 328), for compensating for differences in the positions of the detectors in the matrix. The outputs of the preamplifiers have coupled thereto a selector 22 which comprises, for example, a series of stores, each of which comprises an OR-OR-gate 23. The number of stores corresponds to the number of detector elements to be selected per gamma quantum to be stored. In this preferred embodiment three stores are shown; this corresponds to the number at least required for proper position determination. Depending on the type of camera and the nature of the electronic processing of the measuring pulses, the optimum number may be other than three. The practical number is given by, on the one hand, minimum loss of useful information and, on the other hand, simple and hence quick determination of the parameters of each of the gamma quanta. All pulses are applied, via the gates 23, to a store 24, it being possible to set the gates, for example, such that each pulse which is larger than a previous, already stored pulse replaces the latter pulse. After all pulses, in this case 19, have passed, the three largest thereof will be stored in the store 24.

Each of these stored pulses should contain information as regards the value of the pulse and the position of the detector wherefrom the pulse originates. To this end, the block diagram includes a counting circuit 25 which is coupled to the mechanism for reading pulses from the register 9 and which applies the position information per pulse to the gate 23 which is opened for the relevant pulse.

Using a read circuit 26, the stored pulses are read and applied to a calculating device 27 which determines the value of the scintillation pulse and the position thereof in the scintillation crystal on the basis of the combined data. When an object is scanned by the camera, it is advantageous to arrange a coupling 30 between the calculating device and the scanning mechanism to enable the calculating device to determine the coordinates in the object on the basis of the coordinates in the scintillation crystal. The data determined by the calculating device 27 can be applied to a monitor 28 or a printer 29 for further study. The data can also be stored, for example, in a magnetic storage element.

In a further preferred embodiment use is made of digital techniques for selection and storage by connecting an ADC circuit to each detector. The measuring pulses of the detectors are then available in the form of digital pulses for further processing. A calculating device similar to the calculating device 27 is then provided with a DAC circuit whereby the data are made available and can be displayed in analog form. For the storage in a store, the digital data can also be used. In a further preferred embodiment, use is made of the mixtures of analog and digital techniques, for example, first the pulses of the detectors are thresholded in an analog manner and the further processes are executed in a digital manner. The threshold value can then be adapted again to the nature of the radiation to be measured.

What is claimed is:

1. A scintillation camera comprising a scintillation crystal, a matrix of detectors viewing overlapping areas of said crystal, an output signal being associated with each detector, means for comparing the amplitudes of said output signals and for selecting a predetermined number thereof having the greatest amplitude, and computing circuitry for computing the position of a scintillation produced in said crystal from the selected predetermined number of output signals, thereby to improve spatial resolution by using for position calculation only the information contribution from a predetermined number of detectors situated nearest to the scintillation.

2. A scintillation camera as defined in claim 1 wherein the predetermined number of output signals selected is three.

3. A scintillation camera as defined in claim 1 and further comprising a preamplifier connected to each detector, the compared output signals being the output signals of said preamplifiers.

4. A scintillation camera as defined in claim 3 wherein said preamplifiers compensate for differences in position and gain of said detectors.

5. A scintillation camera as defined in claim 3 wherein said preamplifiers compensate for the nature and energy of the radiation measured by said detectors.

* * * * *